United States Patent [19]

Kugler et al.

[11] Patent Number: 4,719,347

[45] Date of Patent: Jan. 12, 1988

[54] METHOD AND APPARATUS FOR INVESTIGATING A SAMPLE UNDER TENSION

[76] Inventors: Hans-Peter Kugler, Siedlerstr. 34, D-7519 Zaisenhausen; Norbert Eisenreich, Amselstr. 16, D-7507 Pfinztal 1; Adam Geissler, Lachenweg 10, D-7529 Karlsdorf-Neuthard; Klaus Fabry, Goethestrasse 3, D-7519 Walzbachtal, all of Fed. Rep. of Germany

[21] Appl. No.: 812,842

[22] Filed: Dec. 23, 1985

Related U.S. Application Data

[63] Continuation-in-part of Ser. No. 746,096, Jun. 18, 1985.

[30] Foreign Application Priority Data

Mar. 14, 1985 [DE] Fed. Rep. of Germany ....... 3509163

[51] Int. Cl.$^4$ .............................................. G01D 5/34
[52] U.S. Cl. ................................ 250/231 R; 250/560; 73/826
[58] Field of Search ................... 250/231 R, 560, 559, 250/571, 561; 73/800, 826, 1 J, 833, 834; 356/387; 116/212, 270; 33/125 A, 179

[56] References Cited

U.S. PATENT DOCUMENTS

| | | | |
|---|---|---|---|
| 2,670,650 | 3/1954 | Wilmotte | 356/387 |
| 3,592,545 | 7/1971 | Paine | 73/826 |
| 4,031,746 | 6/1977 | Furuta et al. | 73/800 |
| 4,269,514 | 5/1981 | Vassberg | 250/560 |

*Primary Examiner*—David C. Nelms
*Assistant Examiner*—Jessica L. Ruoff
*Attorney, Agent, or Firm*—Antonelli, Terry & Wands

[57] ABSTRACT

A method for investigating a volume change of a sample under tension, with a sample being scanned by a first light beam and the light beam reflected from the sample being detected and further processed. The sample is then illuminated with at least one additional light beam of finite width, with the light beam being converted into a first voltage behind the sample, and a transverse pattern of different reflectivity is scanned by the first light beam longitudinally, and with the change in frequency, produced by stretching, in the reflected light intensity-modulated in this fashion being converted into a corresponding second voltage and the voltages are compared with one another, possibly after calibration.

20 Claims, 9 Drawing Figures

METHOD AND APPARATUS FOR INVESTIGATING A SAMPLE UNDER TENSION

BACKGROUND OF THE INVENTION

This application is a continuation-in-part application of the U.S. application Ser. No. 746,096.

The invention relates to a method and apparatus for investigating a sample under tension, especially a volume change of the sample.

German Auslegeschrift No. 26 31 663 teaches the zero contact measurement of relative changes in length of a sample on the basis of comparative measurements of travel time of laser reflections during continuous scanning of the total measured length of the sample, whereby a light beam is split by a beam splitter, with one portion of the beam of light being directed to the sample and then detected by a photodetector, and the other portion of the beam directed by an adjustable reference diaphragm to a second similar photodetector. Repeated scanning of the zone of different reflectivity of the object being measured is required for evaluation in order to obtain any measurement results at all. For this reason, the method does not exhibit sufficient time resolution and, in particular, does not permit immediate detection of rapid sudden changes in length, so that this method, too, cannot be used for rapid pulling or tearing tests. Moreover, the method allows determination of only an average change in lenght over the total measurement area, and not different stretching behavior in different areas of the sample, especially not the three-dimensional distribution of stretching over the sample, something which is important because a sample is not necessarily subjected to equal changes in length in all of its areas when the same tensile stress is applied, but can exhibit different distributions.

A zero-contact optical measuring method using a cathetometer is described in "Messtechnische Briefe" Vol. 13 No. 2, Page 25-31, 1977 wherein markings made on the samples are scanned with the aid of an optical aiming device by the operator and the distances between the markings are measured by a linear measurement system built into the cathetometer. This is a subjective measuring method involving observation, with the adjustments being made by the operator on the basis of the observation possibly being further automatically processed. The subjective decision on the part of the operator is involved in the measuring process. In addition, the known method does not permit any dynamic pulling tests but only creep tests. In addition, only measurements of lengthwise stretching can be conducted.

The subject of German Auslegeschrift No. 22 34 213 is likewise a subjective method, namely a method for rendering visible the aperiodic elastic deformations of moving bodies, wherein the movements can no longer be observed by periodic flashes of light but rather the light flashes must be adjusted to the aperiodic time curve. A pattern is provided exclusively for this purpose, which achieves synchronization of the pattern markings and the light beams by an adjustable optical system with at least two associated sensors via a logic circuit so that the light flashes can be generated at suitable times in order to carry out the desired subjective stroboscopic observation.

On the basis of the subject of German Auslegeschrift No. 26 31 663 the goal of the invention is to provide a method and an arrangement by which the behavior of a sample under tension, especially the stretching and, contracting behavior and in particular, any volume changes that may occur, can be investigated in a simple and convenient fashion, especially on a mass production basis, whereby the distribution of the stretching behavior of the sample, especially over its length and its behavior especially during rapid pulling and tearing tests, can be investigated.

According to the invention the stated goal is achieved by a method for investigating materials under tension, with a sample being pulled by its ends, with a tensile stress being exerted, and a light beam scanning the sample, with the beam reflected from the sample being picked up by a photoreceiver and processed electronically. The sample, provided with a transverse pattern of different reflectivity or absorptivity, is scanned by the light beam. The invention provides a method for measuring transverse contraction wherein a light beam of finite extent is directed onto the sample and the absolute amount of light is measured behind the sample. It is also provided according to the invention that the sample is scanned with at least one light beam of finite width, with the light beam being converted into a first voltage behind the sample, and a transverse pattern with a different reflectivity applied to the sample is scanned longitudinally by a light beam, and with the change in frequency, caused by stretching in the reflected light intensity-modulated in this fashion being converted into a corresponding second voltage and the latter being compared with the first voltage and the voltages being compared with each other, possibly after calibration.

In accordance with an apparatus according to the invention, a transverse pattern with a different reflectivity or absorptivity is applied to the sample and a lens for rendering parallel the light beams which are, in turn, deflected from the deflecting device and scan the sample, being located beyond the deflecting device. The apparatus is designed especially for measuring the transverse contraction by virtue of the fact that the device for measuring the change in width of the sample comprises a light source located forwardly of the sample with an imaging optical system, as well as a scattering disk and a photosensor located behind the sample on an optical axis which is defined by the light source, the imaging optics, and the sample. In combination, it is provided that an illumination unit with an imaging optical system is provided forwardly of the sample and a first detector, located on the optical axis defined by the light source and the sample, is disposed behind the sample, with the sample having a transverse pattern with a different reflectivity. A light source, a deflecting device between the latter and the sample, and at least one second detector for picking up the light reflected from the sample are provided with a common evaluation device is associated with both detectors.

The optical method according to the invention as well as the optical apparatus initially permit simple, rapid, and accurate measurement of transverse contraction which is nearly insensitive to external influences such as vibrations. The method according to the invention permits making measurements with maximum accuracy and especially resolutions of an average change in width of less than one micron. In view of the simplicity of the method, the latter can also be used in industrial materials testing, where the costly mechanical methods used heretofore were not used since they could only be used in science and research because of their expense, the need for the accuracy of the work, and the time involved, but could not be used for regular monitoring of the manufacture of materials, etc. In addition, in the zero-contact method according to the invention, there is no disadvantageous feedback from the measuring device to the sample. The method according to the invention permits problem-free processing of the measured values using operational amplifiers, since the photodetector arrangement already delivers a DC voltage which is proportional to the measured value. In addition, the method according to the invention can also be used directly in simple fashion for using the measured transverse contraction to control the tensile stress in a system, possibly in the sense of a regulating circuit.

Another advantage of the invention resides in the fact that measurements can be carried out at high stretching rates up to rapid tearing tests, whereby the contraction behavior of materials can be measured in the range of limiting stresses with considerable changes in tensile stress with high accuracy. Moreover, the method according to the invention permits determination of purely elastic behavior, i.e. purely elastic transverse contraction, with high accuracy without requiring extrapolation of the rate-dependent number of transverse contractions, which includes, at low stretching rates, in addition to the component representing the elastic behavior, also one which represents plastic behavior.

Preferred embodiments of the method according to the invention provide for the sample being irradiated with diffusive homogeneous light, and for the light beam striking the sample to be stopped down from a wide light beam. The width of the incident light beam is selected in the direction of the length of the sample such that the roughnesses in the edge area of the sample are averaged out. Another embodiment of the device according to the invention provides for the imaging optics to contain at least one lens which images the light beam from the light source into a parallel beam. Stopping down a suitable narrow light beam is accomplished by the imaging optics including a slit disposed between the sample and the light source and extending transversely to the length of the sample. To study the behavior under tension, for example of a tubular sample or the like, several measurements can be carried out simultaneously from different directions as well.

Th optical method according to the invention as well as the optical device also permits simple, rapid, and accurate measurement of lengthwise stretching, especially also in partial areas, and also the distribution of stretching over the length of the sample, whereby external influences such as vibrations or the like have virtually no effect. The method according to the invention permits measurements to be carried out with maximum accuracy at high resolution, whereby the accuracy of the measurement depends upon the pattern, the scanning rate of the beam, the quality of the detected signal (signal-to-noise ratio) and the electronic processing speed. The scanning frequency, especially when using acousto-optical deflectors, can be in the range of several hundred Kh. The signal received by the receiver and to be processed electronically is a function of the frequency of the light which is intensity-modulated by the lengthwise pattern mounted on the sample, reflected, and received by the photodectector. A considerable advantage resides in the fact that the measurement information is provided as a frequency based on the pattern, since the information is then provided independently of a certain presentation and can be processed further in any suitable fashion. Processing of the received signal can be performed particularly by the multicounting method. Basically however frequency-voltage conversions or processing using inexpensive PLL circuits is also possible, whereby the time-resolution frequency detection, which corresponds to the position resolution stretching can be improved considerably by "high mixing" of a frequency with a medium frequency. If the received signal is used to regulate the pulling speed, the stretching rate can be controlled as a result in a range which is of interest. The method according to the invention also allows measurements in rapid tearing tests with pulling rates on the order of several meters per second, which was previously not possible. With mirror reflection on the sample, the length over which the stretching can be measured is limited by the dimensions of the optical system, especially the radial diameter of the convergent lens located in the reflected beam. If longer stretching lengths are scanned, diffusely reflected light can also be preferably used.

The measurement results are compared in suitable fashion, especially according to the invention, whereby provision can initially be made for the two tensions to be related to the absolute length and width values of the sample and then compared with one another whereupon the resultant measured value is displayed, possibly after averaging. In addition, display devices are advantageously provided so that the two voltages, possibly after electronic processing, are applied to the X and Y inputs of a display, whereby the display is preferably recorded electrooptically on a recorder. The results can also advantageously be stored.

Further features and advantages of the invention are apparent from the claims and from the specification which follows, in which one embodiment is discussed in detail with reference to the acccompanying drawings.

DETAILED DESCRIPTION

Figure 1:
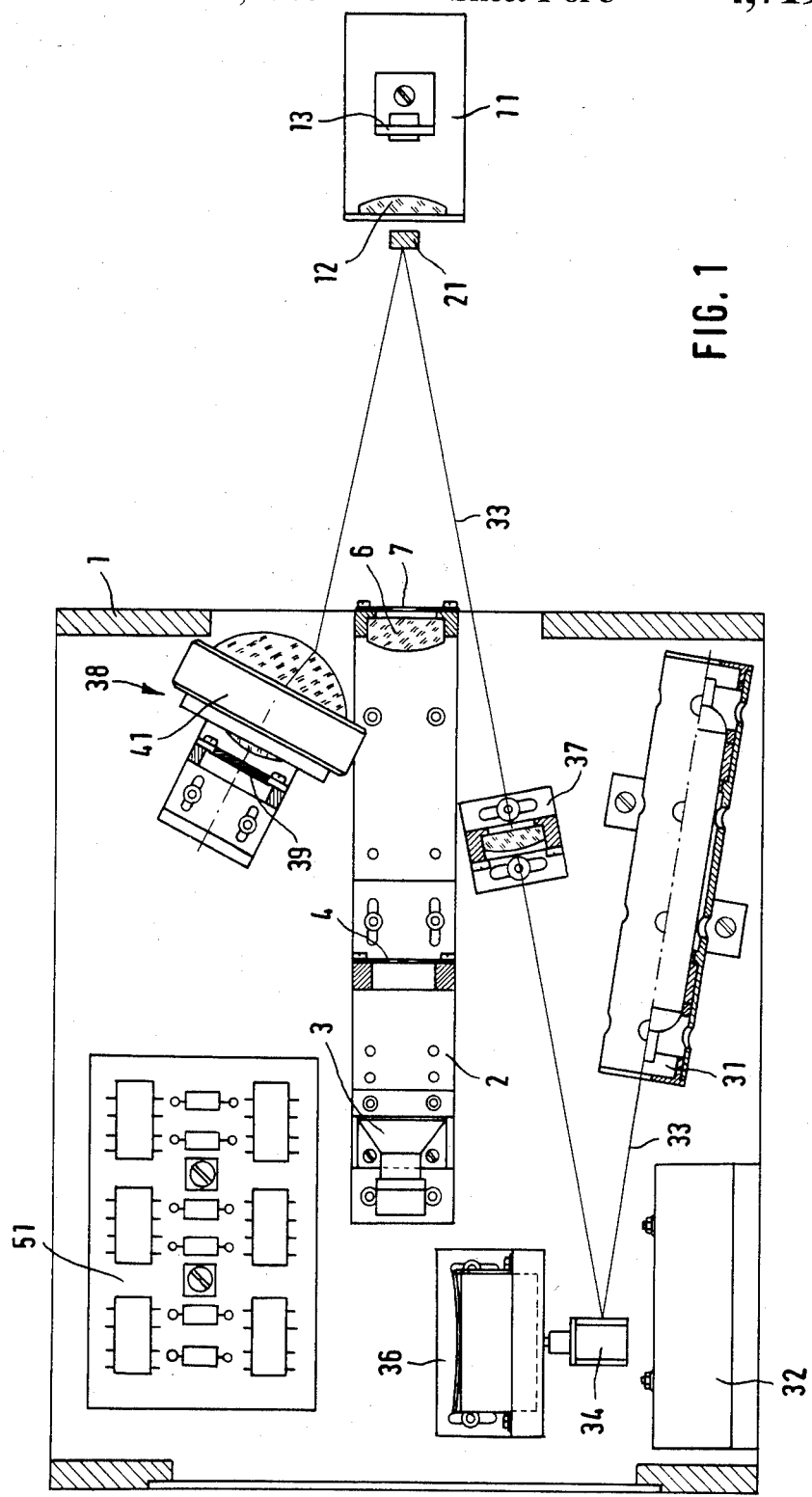
FIG. 1 is a schematic diagram of the measuring arrangement shown in the top view.
Figure 2:
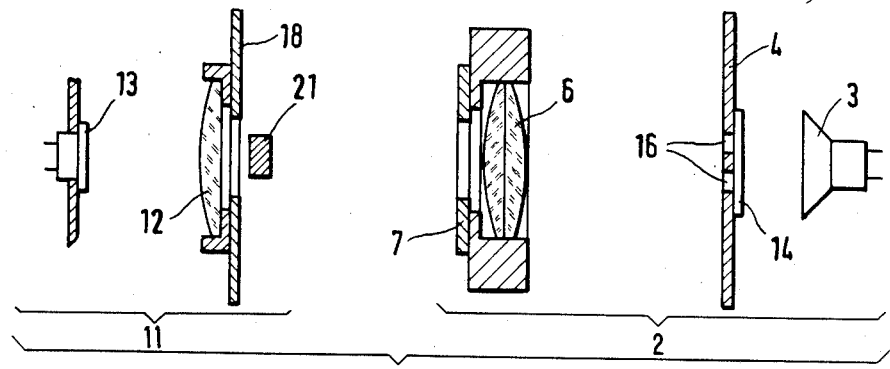
FIG. 2 is the schematic arrangement of the parts used to measure transverse contractions.

According to the invention an apparatus is provided which includes a housing 1 accommodating an illuminating device 2 comprising, for example an ellipsoid lamp 3, a diaphragm 4, preferably with a volume scattering disk, a lens 6, and an exit diaphragm 7. A receiving unit 11 with a shading diaphragm, a focusing lens 12, and a photodiode 13 mounted on a holder are disposed outside of the housing 1 at a distance therefrom on the optical axis determined by the illuminating device 2. The sample under tension 21 is placed between illuminating device 2 and receiving unit 11.

The housing 1 also includes a second illuminating arrangement with another light source in the form of a laser 31 powered by a high-voltage power supply 32. The laser is preferably a helium neon laser with a power of approximately 0.5 mmW having a beam is 0.8 mm in diameter. It is important for the diameter of the beam not to exceed the width of the pattern mounted on sample 21 under tension.

A deflector 34 in the form of a rotating mirror is located in the path of light beam 33 of laser 31, with the rotating mirror being driven by a motor 36. The rotating mirror includes, as a main element thereof a polygon, a precision glass cell for example, whose sides are mirror-coated. The cell, is mounted on the support and, for example, glued thereto. The support is mounted on the shaft of motor 36. In the illustrated embodiment, the motor is a synchronous motor which can be driven by a line voltage of 220 V/50 Hz so that a sufficiently constant rpm can be achieved without considerable expense for regulation, etc. The motor is operated at 500 rpm, resulting in 2000 scans per minute with four mirror faces. Normal pulling tests can be carried out with it. Instead, in a preferred fashion, an rpm-regulated DC motor can be used, which has the important advantage when using different patterns, i.e. different stretching ranges, that the frequency optimized for signal processing can be adjusted as a function of the spacing of the pattern and the motor rpm. In rapid pulling tests, the scanning frequency can be further increased by increasing the rpm and/or the number of mirror faces of the rotating mirror. In addition, especially during rapid tearing tests, other types of deflectors such as, for example, piezoelectric or the like, can be used, which permit very high deflection frequencies.

A cylindrical lens 37 is disposed behind deflector 34 and housing 1 in such fashion that the rotating mirror is located in one of its foci and the sample 21 is preferably located in another focus, so that the approximately parallel laser beam is focused on the surface of the sample.

Figure 3:
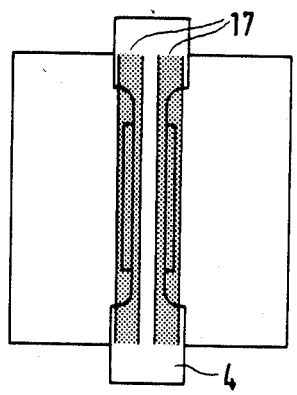
FIG. 3 shows the illumination of the sample under tension by bands of light.
Figure 4:
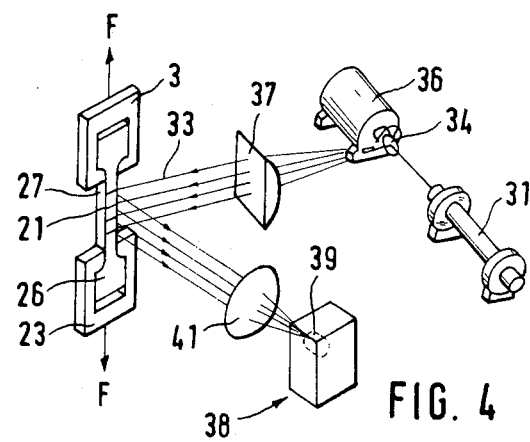
FIG. 4 is a schematic diagram showing part of the arrangement used for measuring lengthwise stretching.

In the given arrangement, the cylindrical lens also causes the light beam to be guided during the scanning produced by the rotating mirror so to speak parallel to itself over the sample under tension beneath the pattern mounted on it. Laser beam 33 is reflected from the pulling sample 21. Accordingly, an additional receiving device 38 is provided in the housing, which has among other things a lens 41 as well as a photodiode 39. The signals detected by the two photodiodes 13 and 39 are fed to an electronic circuit 51 where they are processed in a manner to be described hereinbelow. The light from lamp 3 is diffusely scattered by a volume-scattering disk 14 in such fashion that the intensity of the light illuminating sample 21 is largely homogeneous, in other words every point on the sample is illuminated in the lengthwise and transverse directions with essentially the same light intensity in order to obtain a signal which is as linear as possible. Double diaphragm 4 is associated directly with scattering disk 14, with the diaphragm 4 including two diaphragm slits 16, through which the light from lamp 3 is broken into two partial bands, which are rendered parallel by lens 6, whereby the edges of the light beams can be blocked out by additional diaphragm 7. Accordingly, two light bands 17 (FIG. 3) fall on sample 21 and the shading diaphragm 18 located located directly behind the sample 21. As can be seen from FIG. 3 in particular, the amount of light from the two light bands 17 which passes between sample 21 and shading diaphragm 18 is linearly dependent on the width of the sample, which contracts when the sample is subjected to transverse tension. Calibration can be done if shading diaphragm 18 is adjustable and sample 21 is so adjusted in the relaxed state that no light falls between shading diaphragm 18 and sample 21. The amount of light that passes between sample 21 and shading diaphragm 18 during tension is focused by a focusing lens 12 on photodiode 13 and initially converted into a current which is proportional to the light intensity. The photodiode is biased in the blocking direction whereby the barrier capacitance is simultaneously reduced making possible a more rapid response. By connecting a resistance in series with a photodiode, the photocurrent is converted into a decreasing proportional voltage through the resistor, whereby the value of the resistor determines the sensitivity of the arrangement. The additional electronic circuit initially essentially includes an amplifier and an electrometer subtractor for zero balancing to exclude ambient light.

Figure 5A:
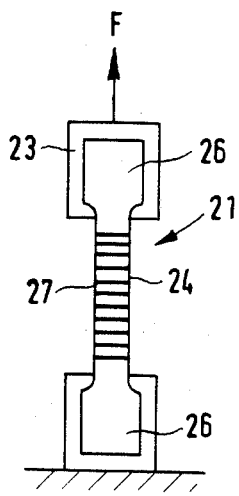
FIG. 5 shows the displacement of the measuring pattern on a sample under tension.
Figure 5B:
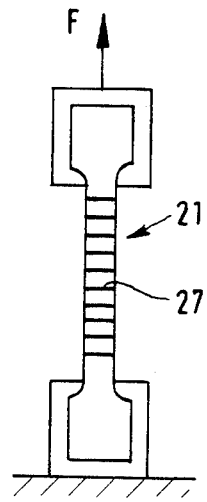

The pulling device, not shown in greater detail, comprises clamping devices 23 for firmly clamping the sample 21. The sample 21 (FIG. 5a) comprises a central part 24 and gripping parts or shoulders 26 which are broadened at both ends thereof, to which shoulders the clamping devices 23 are attached. In addition, a transverse pattern 27 with a different absorptivity and therfore reflectivity or scattering power similar to a bar code, is mounted on one side of the sample 21 in middle part 24. A transverse pattern 27 can be printed, for example, by screen printing. The sample itself consists of any material whose longitudinal stretching in a stretching test is to be investigated, especially in a rapid tearing test. The sample 21 is pulled apart in such a test by a pulling device equipped with clamping devices 23 in the direction of arrrow F. It is evident from a comparision between FIG. 5a and FIG. 5 that the pattern segments increase their spacing as the sample is pulled whereby the frequency of the intensity, modulated by pattern 27, of the reflected light is changed by a beam that uniformly scans the sample, i.e. with constant scanning frequency.

The latter is accomplished by deflector 34, which moves the light beam over the sample 21 along the length of the latter or, in other words, "scans" it over the sample, so that sample 21 and its transverse pattern 27 are scanned by the light beam. Photo detector 39 can be a suitable photodetector such as a photodiode or a photo-FET, connected in the manner described above. Processing electronics 51 can be frequency-selective means, amplifier units and especially a memory device for storing the scanning results received by photoreceiver 13 from scanning transverse pattern 27. It can also include a device for regulating the pulling device and therefore for performing a regulated pulling test.

The test is then performed in such a fashion that, as already mentioned, the pulling device pulls the sample 21 apart by the clamping devices 23 in a longitudinal direction of the sample 21, and the sample 21 is therefore stretched in the process. The relative strength Δd (FIG. 1b) is then greater in a middle portion of the sample than in a marginal part of the sample 21 near the gripping parts or shoulder pieces 26. More particularly, with suitable materials, with a rapid tearing test on the sample 21, a tension drop, in other words, a drop in the strength of the sample 21, can occur locally in this area as can an unsteady further stretching produced thereby, whereupon stretching then remains limited to this area until a breakage finally occurs.

During the stretching of the sample 21 by the pulling device the sample, more specifically, the transverse pattern 27 thereof, is repeatedly scanned in the longitudinal direction by the beam 33 by the deflector 34. The scanning rate of deflected beam 33 is much greater than the pulling speed. While the pulling speed, for example, with a regulated rapid tearing test, is on the order of 10 to 15 m/s and, for normal stretching test, on the order of 5 cm/s or per minute, the sample is scanned longitudinally with a relatively high frequency of 50 to 100 Hz with a rotating mirror up to between 100 kHz and the megahertz range in the case of an acousto-optical deflector. Then, because of the pattern 27, which alternately largely absorbs and diffusely reflects the light, etc., a light which is intensity-modulated at a high frequency is received by photoreceiver 14 whereby the frequency of the intensity modulation is determined by the scanning frequency and the spacing of lines 28 of the transverse pattern 27. If the sample is now pulled apart in the pulling test, the spacing of the lines 28 in the transverse pattern 27 changes and so does the frequency of the intensity modulation received by the photoreceiver 39, so that this change in frequency contains the information about the longitudinal stretching behavior of the sample 21 during the pulling test.

Figure 6A:
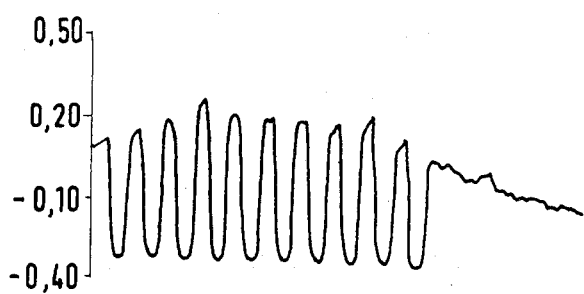
FIG. 6 shows the intensity of the reflected light: (a) without stretching, (b) at a stretching of about 10%, (c) the signal of (b) after further shaping.
Figure 6B:
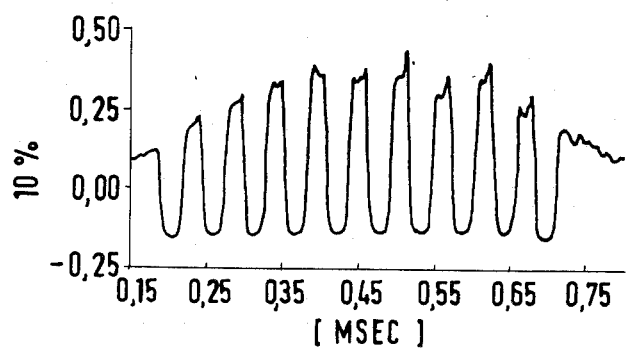
Figure 6C:
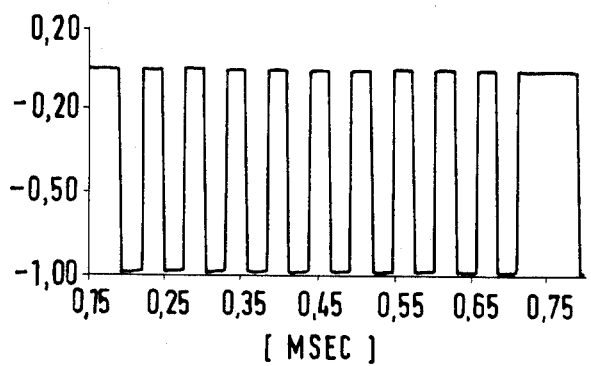

The signal from photodiode 39 can include a noise component caused by ambient light, such as daylight or artificial light which is filtered out by an optical filter located in front of the photoreceiver or an electrical filter located behind the receiver, so that only the signal from the pulling test is passed. This is shown for a sample without tension in FIG. 6a and for the same sample under tension in FIG. 6b. So long as the relative change in stress $\Delta d$ is not greater than the total length of the sample, the procedure according to the invention allows determination of this stretching behavior which differs over the length by different frequencies of intensity modulation. The signal which is received by the receiver and processed further by the electronics is, in the longitudinal stretching measurement, the frequency of the intensity-modulated light which is directly proportional to the spacing of the lines in the pattern. The signal is shaped into a square-wave train by a Schmitt trigger for example (FIG. 6c). Further processing can include, in addition to a Fourier transform of the frequency signal by a computer, a frequency-voltage conversion or digital counting in the multicounting method, whereby the second method named is simpler in principle and the digital conversion is employed especially at high speeds. In the multicounting method, counters connected to a high-frequency oscillator are started in common by the leading edge of a first wave and stopped successively by the flanks of following waves or pulses. The counter information can be stored directly in the memory of a computer and then processed further. A simple and economical frequency-voltage demodulation can also be provided by a PLL circuit. In this case, the phase position of the measured signal is compared with that of a voltage-controlled reference oscillator (VCO) and retraced from the phase difference by means of a suitable regulating circuit of the VCO. The control voltage is proportional to the frequency of the signal in the VCO in the capture range of the PLL. Another processing capability incorporates a monoflop with an integrator connected in series on the consumer side. The measured voltage measured value is stored by a hold circuit, for example in the form with a peak meter. Other elements can be analog subtractors, etc. for zero adjustment. The voltage values of the longitudinal stretching and transverse contraction measurement can be supplied for evaluation directly to the X and Y inputs of an oscillograph or a recorder. After division by a value that represents the absolute length or width, the ratio of the relative transverse contraction and longitudinal stretching can be determined for determining the number of transverse contractions either electronically or by an oscillograph or recorder on the basis of the indicated slope.

To the extent that light has been mentioned above, preferably visible light is meant, but invisible light can also be used. The method according to the invention and the apparatus according to the invention provide a simple and convenient way of determining the longitudinal stretching of a sample especially in quick tearing tests, wherein the conventional primarily mechanical scanners are too slow. In addition, a regulated pulling test can be performed whereby not the adjustment of the speed on the pulling machine itself but the regulation of the pulling speed of the sample itself in a characteristic range is meant. The method and apparatus according to the invention can be advantageously used for regular materials tested in industrial laboratories. The method according to the invention allows carrying out tearing tests in simple fashion with high accuracy of observation of the relevant values over the entire tearing process. In addition, likewise in a simple and convenient fashion, the number of transverse contractions for different materials can be measured on a mass production basis without high expense.

The features of the invention disclosed in the above specification, in the drawings, and in the claims can be important both individually and in suitable combinations for working the invention in its various embodiments.

We claim:

1. Method for investigating a volume change of a sample under tension, the method comprising the steps of:
   scanning the sample by a first light beam,
   detecting the light beam reflecting from the sample and further processing the detected reflected light beam,
   irradiating the sample by at least one additional light beam of a finite width,
   converting the light beam into a first voltage behind the sample,
   scanning a transverse pattern with a different reflectivity mounted on the sample by the first light beam in a longitudinal direction,
   converting a change in frequency caused by stretching of the sample in the reflected light thus intensity-modulated into a corresponding second voltage, and
   comparing the first and second voltages with each other.

2. Method according to claim 1, wherein the step of irradiating the sample comprises providing a light beam of a finite width of diffuse homogeneous light.

3. Method according to claim 1, wherein the light beam striking the sample is of a finite width and is blocked out from a wider light beam.

4. Method according to claim 1, wherein the light beam is composed of two bands of light.

5. Method according to claim 1, further comprising the step of measuring the sample to regulate a pulling of the sample for carrying out a regulated pulling test.

6. Method according to claim 1, wherein the step of comparing includes placing the first and second voltages in a relationship to an absolute length of the sample and width of the sample, and then comparing the first and second voltages with each other.

7. Method according to claim 6, further comprising the step of displaying a resultant measured value of the sample, after an averaging.

8. Method according to claim 1, further comprising the steps of electronic processing of the first and second voltages, and applying the processed voltages to X and Y inputs of a display.

9. An apparatus for investigating a material under tension, with a pulling device and a measuring device, the apparatus comprising a light source, at least one photoreceiver disposed in front of a sample of the material, a deflecting device provided between the light source and the sample of the material, a transverse pattern with a different reflectivity or absorptivity is mounted on the sample of the material, and a lens means for rendering light beams repeatedly deflected from the deflector device and scanning the sample of the material are rendered parallel.

10. An apparatus for investigating a volume change of a sample under tension, with a pulling device and at least one measuring device, the apparatus comprising at least one light source, a first detector associated with the sample, a deflector disposed between the at least one light source and the sample, a transverse pattern with different reflectivity provided on the sample, said transverse pattern being scannable by the light from the first light source by deflector means, an illuminating unit with an imaging optical system is located in front of the sample and a second detector is located along an axis defined by the illuminating unit and the sample, and a common evaluating device is operatively associated with said first and second detectors.

11. An apparatus according to one of claims 9 to 10, wherein the deflecting means comprises an acousto-optical deflector.

12. An apparatus according to one of claims 9 to 10, wherein the deflector means comprises one of a rotating mirror, a tilting mirror, or a rotating prism.

13. An apparatus according to one of claims 9 to 10, further comprising a filter arrangement provided forwardly of the second detector.

14. An apparatus according to one of claims 9 to 10, wherein the electronic evaluating device is connected to a pulling device for regulating the pulling of the sample.

15. An appparatus according to claim 10, wherein the evaluating device incorporates circuit elements for determining the relative value of measured parameters as a function of output measurements of the sample represented by reference values.

16. An apparatus according to claim 10, further comprising divider means for dividing measured values of the first and second detectors, and display means for displaying a resultant value.

17. An apparatus for measuring a lateral contraction of a test piece having a transverse pattern with a reflectivity differing from the test piece elongated by a drawing device including a device for measuring a lateral contraction of the test piece, the apparatus comprising a light source means arranged upstream of the test piece, said light source means including imaging optic means, a diaphragm plate means disposed downstream of the test piece for defining a narrow strip of light from the light source means, and a light detector means positioned downstream of the diaphragm and disposed on an optical axis defined by the light source means, the imaging optic means, and the test piece.

18. An apparatus according to claim 17, wherein the imaging optic means includes at least one lens means for imaging a light beam of a light source means in a parallel beam.

19. An apparatus according to one of claims 17 or 18, wherein the imaging optic means has a slit extending at right angles to a longitudinal extension of the test piece and positioned between the test piece and the light source means.

20. An apparatus according to one of claims 17 or 18, wherein a slit means is provided for blocking the light from the light source means, and wherein the imaging optic means includes a cylindrical lens means for imaging the slit means on a plane of the test piece.

* * * * *